United States Patent [19]

Soler et al.

[11] Patent Number: 6,113,926
[45] Date of Patent: Sep. 5, 2000

[54] COMPOSITION AND TOPICAL FORMULATION OF ANTIANDROGENS OF NATURAL (PLANT) ORIGIN

[76] Inventors: José Cabo Soler; Juan Bautista Peris Gisbert, both of Avenida Barón de Carcer, 46-24, E-46001 Valencia, Spain

[21] Appl. No.: 08/817,146

[22] PCT Filed: Aug. 8, 1996

[86] PCT No.: PCT/ES96/00158

§ 371 Date: Jun. 19, 1997

§ 102(e) Date: Jun. 19, 1997

[87] PCT Pub. No.: WO97/05887

PCT Pub. Date: Feb. 20, 1997

[30] Foreign Application Priority Data

Aug. 9, 1995 [ES] Spain ....................................... 9501629

[51] Int. Cl.[7] ............................... A61K 6/00; A61K 7/00; A61K 7/06; A01N 65/00

[52] U.S. Cl. ........................ 424/401; 424/74; 424/195.1
[58] Field of Search ................................... 424/401, 70.1, 424/195.1, 74

[56] References Cited

U.S. PATENT DOCUMENTS 4,569,839  2/1986  Grollier et al. ............................ 424/74
5,641,480  6/1997  Vermeer ................................ 424/70.24

*Primary Examiner*—Thurman K. Page
*Assistant Examiner*—Sharon Howard
*Attorney, Agent, or Firm*—Sterne, Kessler, Goldstein & Fox, P.L.L.C.

[57] ABSTRACT

A composition consisting essentially of a plant extract rich in antiandrogenic sterols from dwarfpalms, African plums, willow herbs, nettle herbs, or hops. The composition can be combined with an acceptable carrier agent to form a variety of topical formulations for cosmetic and pharmaceutical purposes.

15 Claims, No Drawings

COMPOSITION AND TOPICAL FORMULATION OF ANTIANDROGENS OF NATURAL (PLANT) ORIGIN

TECHNICAL SPHERE OF THE INVENTION

The present invention fits in the technical sphere of hormonal and/or antihormonal therapy, destinated to the maintenance of certain functions and structures that deteriorate with aging or due to other reasons and the treatment of several metabolic or degenerative illnesses and control of the growth, aspect, development and/or growth of certain structures, such as hair (excess or loss), corporal hair, prostate, skin and its problems (acne, rosacea . . . ), etc. which are influenced by the sex hormones levels (androgens and estrogens).

More exactly, the present invention refers to a new form of presentation for phytosterols with antiandrogenic action destinated to percutaneous topical application with cosmetic and/or pharmaceutical purposes.

STATE OF THE TECHNIC PREVIOUS TO THE INVENTION

The natural serols present and extracted from vegetal drugs, such as:

Serenoa sp. pl. Fam. Palmaccae. Spanish denomination: Sabal, palmeras de Florida, de Tejas y de Cuba. English den . . . Dwarfpalm. French Den.: Sabals, Serénoas. German Den.: Zwergpalmes, Sagepalmes. Italian Den.: Sabali.

Pygeum sp. pl. Fam. Rosaceae. Spanish Denomination: Ciruelos africanos. English Den.: African plums, French Den.: Pruniers d'Afrique. Italian Den.: Prune di Africa.

Epilobium sp. pl. Fam. Oenoteraccae. Spanish denomination: Epliobios. English Den.: Willow herbs, Rosebay. French Den.: Epliobes. German Den.: Waldröschens. Italian Den.: Epilobii.

Urtica dioica L. y Urtica sp. pl. Fam. Urticaceae. Spanish denomination: Ortigas mayores. English Den.: Nettle herbs, urtica y stinging nettles. German Den.: Brennesselkrauts, Haarnesselkrauts, Hanfnesselkrauts. French Den.: Herbes d'ortie. Italian Den.: Ortiche.

Hypoxis, sp. pl., specially the root of the Hypoxis rooperi and Hypoxis brasiliensis.

Cucurbita, sp. pl., Fam. Cucurbitaceae, specially the seeds of Curcurbita pepo y Cucurbita máxima (spanish, popular denomination: calabazas).

And other vegetal products such as bitter resins present in the strobila of Hop (*Humulus lupulus* L.; Fam Cannabaceao), also with antiandrogenic action are used in medicine orally for the treatment of prostate benign hypertrophy and other prostatic problems, femenin hirsutism and virilism.

Several of the vegetal extracts, rich in phytosterols, mentioned before, are being used orally as pharmaceutical specialities for the treatment of prostatic benign hypertrophy (Adriazola et al., 1992, Di-Silverio et al., 1992, Vahlensiek et al., 1993, Timmermans et al., 1990, Muhlbauer, 1991, Breu et al., 1992 y Sultan et al, 1984).

DESCRIPTION IN DETAIL OF THE INVENTION

The present invention, as exposed before, makes reference to a new cosmetic and pharmaceutical formulation based on extracts and galenic concentrates from vegetal drugs rich in sterols and/or others compounds (resins, etc.) with antiandrogenic action, for their percutaneous topical application.

The applicant has been able to verify, through his investigations, that the active principes of these vegetal drugs and specially the phytosterols and resin, etc. are absorbed well topically, mainly percutaneously.

Therefore, and accordingly to this finding, the inventors propose a novel cosmetic or pharmaceutical formule of presentation (topical) of these vegetal extracts, that we following enumerate:

Glycolic extracts of Dwarfpalms, of African plums, of Willow herbs, of Nettle herbs and of Hops.

Glyceric extracts of Dwarfpalms, of African plums, of Willow gerbs, of Nettle herbs and of Hops.

Hydroalcoholic extracts of Dwarfpalms, African plums, of Willow herbs, of Nettle herbs or Hops.

Lipidic-sterolic extracts of Dwarfpalms, of African plums, of Willow herbs, of Nettle herbs and of Hops.

Acetic extracts (vinegars) of Dwarfpalms, of African plums, of Willow herbs, of Nettle herbs and of Hops.

Chloroformic and ethereal extracts of Dwarfpalms, of African plums, of Willow herbs, of Nettle herbs and of Hops.

Dry extracts (and soft) of Dwarfpalms, of African plums, of Willow herbs, of Nettle herbs and of Hops.

All these extracts, individually or combined, would became part of different preparations for topical application, such as gels, O/W and W/O emulsions, solutions or ointments for percutaneous application with cosmetic or pharmaceutical purposes.

This type of applications allows to reach topically the more convenient levels of these vegetal principles for each problem.

The new formulation of the invention is characterized for containing as essential ingredients for COSMETICS:

a) Between 0.1 and 10% of glycolic or glyceric extracts or oleates of Dwarfpalms, of African plums, of Willow herbs, of Nettle herbs and of Hops.

b) As acrylic gel (Carbopol between 0.5 and 3%), gels derived from guar-gum (Between 1 and 3%), gels derivated from cellulose (from 1 to 5%), o/w emulsions (specially with L-200 base, between 12 and 18%, purcelin oil, between 18 and 25%), w/o emulsions (specially Cold-Cream) and hydroalcoholic, hydropropylenglycolic, hydroglyceroalcoholic solutions with an alcoholic content between 3 and 80° and hydroglycolic solutions.

Besides these ingredients a) and b), these formulations can contain serera vegetal extracts with cooperating or complementary effects, which could be glycolic, hydroglycerolic, hydroalcoholic and hydropropylenglycolic extracts, in proportions between 0.1 and 20% menthol, mentil lactate, mint essence, etc.); Astrigent vasoconstricting extracts of Witch-hazel, Ladies' mantle and Rantany; Demulcent extracts of Aloe, Oats, Althea, Camomile, Yarrow and Mallow: Antiseptic extracts of Hops and other active ingredients; anti-free radicals (tocopherols, between 0.05 and 0.1%, L-ascorbic acid, between 0.1 and 5%, cytoflavonoids, between 0.1 and 2%); antiinflammatories: Allantoin and derivatives (between 0.05 and 0.2%), alfabisalobol, between 0.05 and 0.2%, azulene and derivatives (between 0.05 and 0.2%); antisweating agents: Aluminium salts, specially Aluminium clorhydroxide between 0.1 and 5% and desiccated aluminium hydroxide collodial gel, between 0.1 and 10% and the glycolic, glyceric or fluid extract of Sage, between 0.1 and 5%; vegetal proteolytic enzymes, specially papain between 0.1 and 2%, bromelain, between 0.1 and 0.5%; antialopecia products, such as progesterone (between 1 and 3%) minoxidil (from 1–3%), tricopeptides (0.01–2%) and tricosacarides (0.1–2%), hair decolorants, specially mandarin essential oil (0.5–5%) and other hair growth retarding substances, such as alkyl-isoquinoleine bromide (0.2–3%).

The new formulation of the invention is characterized for its composition as essential ingredients for PHARMACY:
a) Between 0.1 and 100% of glycolic extracts of de Dwarfpalms, African plum, Willow herbs, Nettle herbs and Hops. Between 0.1 and 30% of fluid extract of Dwarfpalm, of African plum, of Willow herb, of Nettle herb and of Hops, or between 0.1 and 100% of glyceric extracts and oleates of the same vegetals. Lipidic-sterolic extracts between 0.01 and 2% or dried extracts, between 0.1 and 4%.
b) As acrylic gel (Carbopol between 0.5 and 3%), Guar-gum derivated gels (from 1 to 3%), cellulose derivated gels from 1 to 5%) o/w emulsions (specially with L-200 base, between 12 and 18%, purcelin oil, between 18 and 25%), w/o emulsions (specially Cold Cream), hydroalcoholic, hydropropylenalcoholic, and hydroglyerolalcoholic solutions with and alcoholic content between 3 and 80° and hydroglycolic solutions.

Besides these ingredients a) and b), these formulations can contain several vegetal extracts with cooperating or complementary effects, which could be glycolic, hydroglycerolic, hydroalcoholic and hydropropylenglycolic extracts, in proportion between 0.1 and 20%: Antipruriginous extracts of Centella Asiatica and of Mint and derivatives (asiaticosides, menthol, menthil lactate, mint essence, etc.); Astrigent vasoconstricting extracts of Witch-hazel, Ladies' mantle, and Rantnay; domulcent extracts of Aloe, Oats, Althea, Camomile, Yarrow and Mallow (between 1–15%); Antiseptic extracts of Hops (0.1–10%) and other active ingredients:anti-free radicals (tocopherols, between 0.05 and 0.1%, L-ascorbic acid, between 0.1 and 5%, cytoflavonoids, between 0.1 and 2%); antiinflammatories: Allantoin and derivatives (between 0.05 and 0.2%), alfa-bisalobol, between 0.05 and 0.2%, azulene and derivatives (between 0.05 and 0.2%); corticosteroids (between 0.01 and 0.1%); bencidamine Cl' (0.1–0.2%) antisweating agents: Aluminium salts, specially Aluminium clorhydroxide between 0.1 and 5% and desiceated aluminium hydroxide collodial gel, between 0.1 and 10% and the glycolic, glyceric or fluide extract of Sage, between 0.1 and 5%; vegetal proteolytic enzymes, specially papain between 0.1 and 2%, bromclain, between 0.1 and 0.5%; antialopecia products, such as progesterone (between 1 and 3%), minoxidil (from 1–3%), tricopeptides (0.01–2%) and tricosacarides (0.1–2%, hair decolorants, specially mandarin essential oil (0.5–5%) and basic hydroquinone (1–3%); topical use antibiotics, specially basic erythromicin (1–3%), and clindamicin (0.5–1%); Keratolytic_reducing agents, such as salicylic acid and derivatives (0.1–3%), benzoyl peroxide (2.5–10%) and resorcinol (0.1–0.5%); chemical depilatories, such as thioglycolic acid and its salts (3–10%) and the association with other chemical antiandrogens (cyproterone acetate. Flutemide and Finastiride. Casodex, etc. between 0.01 and 2%) and other hair growth retarding substances, such as alkyl-soquinoleine bromide (0.2–5%).

Forms of Performing the Invention

The present invention is illustrated besides by mean of the following examples, that do not limit its possibilities: COSMETICS

EXAMPLE 1

In this part we show several formulations according to the present invention, indicating the quantities of active ingredients used and the application to which they are thought for.

Formulation 1
 Glycolic extract of Willow herbs or of nettle herbs roots or of dwarfpalms or of African plums 7–10%
 Alantoin 0.1%
 Colorless fluid extract of witch-hazel 10%
 alfa-Bisalobol 0.1%
 Essential Camomile oil 1%
 Essential Mandarin oil 2%
 L-Ascorbic Acid 0.2%
 Wheat germ oil 3%
 Menthil Lactate 0.05%
 Hops fluid extract 2%
 Acrylic Gel (of Carbopol), sufficient quantity for (csp) 100 g This formulation is useful for the control and retardation of hair growth; this formulation can be also prepared as an hydroalcoholic solution form.

Formulation 2
 Glycolic extract of Willow herbs or of nettle herbs roots or of dwarfpalms or of African plums 5–7%
 Desiccated Aluminum hydroxide Gel 5%
 Hops glycolic extract 2–3%
 Oats glycolic extract 5%
 Plantain glycolic extract 2%
 Glycolic extract of Althea 2%
 Roses distilled water 10%
 Lavender essential oil 2%
 Alantoin 0.1%
 alfa-Bisalobol 0.1%
 Colorless fluid extract of Witch-hazel 5%
 Glycolic extract of Centella 2%
 Acrylic gel (of Carbopol), csp 100 g This formulation is useful to control the odor and axillary sweating, besides controlling and retarding the growth of axillary hair. This formulation can be also presented as an hydroalcoholic solution form.

Formulación 3
 Glycolic extract of Willow herbs or of nettle herbs roots or of dwarfpalms or of African plums 5–8%
 Hops glycolic extract 2%
 plantain glycolic extract 3%
 Oat glycolic extract 3%
 Glycolic extract of Althea 3%
 Colorless fluid extract of Witch-hazel 5–10%
 Ulmaria fluid extract 2%
 Alantoin 0.1%
 Roses distilled water 10%
 70° alcohol, csp 100 g this formulation is useful for controlling hirsutism and acne vulgaris. It can also be presented as a gel (Carbopol or hydroxipropil Guar-Gum).

Formulation 4
 Glycolic extract of Nettle herb roots or Willow herb 10%
 Tricopeptides 0.1%
 Minoxidil 1%
 alfa-Bisalobol 0.1%
 Hydroalcoholic solución, csp 100 g This formulation is useful for control and retardation of hair loss in certain androgenic alopeciae. This formulation can be also presented as a shampoo (anionic sulfonate detergent, csp 100 g).

Pharmaceutical Applications

The present invention is shown additionally by mean of the following examples, that do not limit its scope:

EXAMPLE 2

In this example we show several formulations according to the present invention, indicating the quantities of active ingredients used and their applications:

Formulación 1

Glycolic extract of Willow herbs or roots of Nettle herbs or of Dwarfpalms or of African plum 8–100%
L-Ascorbic acid, csp (as anti-free radicals)

This formulation is useful for treating hirsutism.

Formulation 2

Fluid extract of Willow herbs or roots of Nettle herbs or of Dwarfpalms or of African plum 8–25%
L-Ascorbic acid 0.5%
Colorless fluid extract of Witch-hazel 10%
Menthil lactate 0.1%
Wheat germ oil 3%
alfa-Bisalobol 0.1%
Alantoin 0.1%
Mandarin essence 2%
Camomile extract 2%
Hops fluid extract 1%
Acrylic gel (of Cabopol), csp 100 g This formulation is useful in the treatment of hirsutism. It can also be formulated as an hydroalcoholic solution and in case it is used immediately after depilation it can contain papain from 0.5 to 1%.

Formulation 3

Lipidic-sterolic extract of Willow herbs or roots of Nettle herbs or of Dwarfpalms or of African plum 0.2%
alfa-Bisalobol 0.1%
Alantoin 0.1%
Camomile essential oil 1%
Mandarin essential 2%
Colorless fluid extract of Witch-hazel 5%
Hops fluid extract 1%
Acrylic gel (of Carbopol), csp 100 g This formulation is useful for the treatment of hirsutism and of bening prostatic adenoma (topical use).

Formulation 4

Glycolic extracts of Willow herbs or roots of Nettle herbs or of Dwarfpalms or of African plum 5%
Erythromicin base 2%
L-Ascorbic acid 0.5%
Glycolic extract of Plantain 3%
Elder-tree distilled water 5%
Hops fluid extract 1%
Hydroalcoholic solution, csp 100 g This formulation is useful for treating acne vulgaris and rosacea acne.

Formulation 5

Fluid extract of Willow herbs or roots of Nettle herbs of Dwarfpalms or of African plum 7%
Benzoyl peroxide 5%
L-Ascorbic acid 0.2%
alfa-Bisalobol 0.1%
Glycolic extract of Aloe 3%
Glycolic extract of Althea 3%
Hops fluid extract 1%
Acrylic gel (of Carbopol, csp 100 g This formulation is useful for treating acne.

Formulation 6

Fluid extract of Willow herbs or roots of Nettle herbs of Dwarfpalms or of African plum 10%
Benzoyl peroxide 5%
L-Ascorbic acid 0.3%
alfa-Bisalobol 0.1%
Glycolic extract of Plantain 5%
Oat glycolic extract 10%
Glycolic extract of Althea 5%
Triamcianolone acetonide 0.05%
Hops glycolic extract 1%
Acrylic gel (of Carbopol), csp 100 g This formulation is useful for treating acne.

Formulation 7

Fluid extract of Willow herbs or roots of Nettle herbs of Dwarfpalms or of African plum 5–10%
Clindamicine 1%
L-Ascorbic acid 0.2%
Glycolic extract of Althea 5%
Menthil lactate 0.1%
Hops glycolic extract 1%
Acrylic gel (of Carbopol) or hydroalcoholic solution, csp 100 g This formulation is useful for treating acne.

L-Ascorbic acid 0.2%
Glycolic extract of Althea 5%
Menthil lactate 0.1%
Hops glycolic extract 1%
Acrylic gel (of Carbopol) or hydroalcoholic solution, csp 100 g This formulation is useful for treating acne.

What is claimed is:

1. A topical formulation comprising about 10% by weight of a glycolic plant extract rich in antiandrogenic sterols selected from a group consisting of nettle herb roots or willow herbs in combination with a cosmetically acceptable vehicle and further in combination with an antialopecia agent.

2. The cosmetic of claim 1, wherein said cosmetically acceptable vehicle is a hydroalcoholic solution.

3. A cosmetic for topical application to the skin to control and retard hair loss, comprising about 10% by weight of a glycolic plant extract rich in antiandrogenic sterols selected from a group consisting of nettle herb roots and willow herbs in combination with a cosmetically acceptable carrier and an antialopecia agent.

4. A method for treating a subject with hirsutism comprising the step of:
administering a therapeutically effective amount of a transdermal medicament comprising a topical formulation including a plant extract rich in antiandrogenic sterols selected from a group consisting of willow herbs, nettle herb roots, dwarfpalms or African plums in combination with a carrier agent to an affected area of the subject.

5. A method for controlling and retarding hair loss in a subject comprising the step of:

administering a topical formulation comprising a plant extract rich in antiandrogenic sterols selected from a group consisting of nettle herb roots or willow herbs in combination with a cosmetically acceptable vehicle to an affected area of the subject.

6. A method for controlling and retarding hair growth in a subject comprising the step of:

administering a topical formulation comprising a plant extract rich in antiandrogenic sterols selected from a group consisting of willow herbs, nettle herb roots, dwarfpalms, or African plums in combination with a cosmetically acceptable vehicle to an affected area of the subject.

7. The method for treating a subject with hirsutism according to claim 4, wherein said transdermal medicament comprises from about 8 to 100% by weight of said plant extract and wherein said plant extract is glycolic.

8. The method for treating a subject with hirsutism according to claim 4, wherein said transdermal medicament comprises from about 8 to 25% by weight of said plant extract and wherein said plant extract is fluidic.

9. The method for treating a subject with hirsutism according to claim 4, wherein said transdermal medicament comprises about 0.2% to 2% by weight of said plant extract and wherein said plant extract is lipidic-sterolic.

10. The method for controlling and retarding hair loss in a subject according to claim 5, wherein said topical formulation comprises about 10% to 20% by weight of said plant extract and wherein said plant extract is glycolic.

11. The method for controlling and retarding hair loss in a subject according to claim 10, wherein said topical formulation is further in combination with an antialopecia agent.

12. The method for controlling and retarding hair loss in a subject according to claim 11, wherein said cosmetically acceptable vehicle is a hydroalcoholic solution.

13. A method for controlling and retarding hair loss in a subject comprising the step of:

administering a cosmetic for topical application to the skin comprising about 10% to 20% by weight of a glycolic plant extract rich in antiandrogenic sterols selected from a group consisting of nettle herb roots and willow herbs in combination with a cosmetically acceptable vehicle and an antialopecia agent to an affected area of the subject.

14. The method for controlling and retarding hair growth in a subject according to claim 6, wherein said topical formulation comprises about 7 to 10% by weight of said plant extract and wherein said plant extract is glycolic.

15. The method for controlling and retarding hair growth in a subject according to claim 14, wherein said cosmetically acceptable vehicle is an acrylic gel or a cream.

* * * * *